United States Patent
Choi et al.

(10) Patent No.: US 9,441,257 B2
(45) Date of Patent: Sep. 13, 2016

(54) METHOD FOR PRODUCING FERMENTED EDIBLE PLANTS OR EDIBLE ANIMAL/PLANTS, FERMENTED EDIBLE PLANTS OR EDIBLE ANIMAL/PLANTS PRODUCED BY SAME, AND FOODS CONTAINING SAME

(75) Inventors: Joo Chae Choi, Seoul (KR); Jun Han Choi, Seoul (KR); Seung Han Choi, Seoul (KR)

(73) Assignee: PHARVIS R&D KOREA CO., LTD., Seoul (KR)

( * ) Notice: Subject to any disclaimer, the term of this patent is extended or adjusted under 35 U.S.C. 154(b) by 1186 days.

(21) Appl. No.: 12/918,283

(22) PCT Filed: May 6, 2009

(86) PCT No.: PCT/KR2009/002372
§ 371 (c)(1),
(2), (4) Date: Aug. 18, 2010

(87) PCT Pub. No.: WO2010/024514
PCT Pub. Date: Mar. 4, 2010

(65) Prior Publication Data
US 2010/0316763 A1    Dec. 16, 2010

(30) Foreign Application Priority Data

Aug. 29, 2008 (KR) .................. 10-2008-0084956
Aug. 29, 2008 (KR) .................. 10-2008-0084968

(51) Int. Cl.
*C12P 39/00* (2006.01)
*A23L 1/105* (2006.01)
(Continued)

(52) U.S. Cl.
CPC ............... *C12P 39/00* (2013.01); *A23K 10/12* (2016.05); *A23L 1/105* (2013.01); *A23L 1/2008* (2013.01);
(Continued)

(58) Field of Classification Search
CPC .................. A23L 2/84; A23L 2/382
USPC .................. 426/61, 62
See application file for complete search history.

(56) References Cited

U.S. PATENT DOCUMENTS

| | | | |
|---|---|---|---|
| 4,428,968 A * | 1/1984 | Hsu et al. ............. | 426/49 |
| 2004/0146600 A1* | 7/2004 | Schlothauer et al. ........... | 426/7 |

(Continued)

FOREIGN PATENT DOCUMENTS

| | | |
|---|---|---|
| DE | 2440536 A1 | 7/1975 |
| EP | 0357320 A2 | 3/1990 |

(Continued)

OTHER PUBLICATIONS

Supplementary European Search Report issued in EP Appln. No. 09810119 on Jan. 30, 2012, 5 pages.
(Continued)

*Primary Examiner* — Nikki H Dees
*Assistant Examiner* — Amber Cox
(74) *Attorney, Agent, or Firm* — Rothwell, Figg, Ernst & Manbeck, P.C.

(57) ABSTRACT

A method for producing fermented edible plants alone or a mixture of edible plants and edible animals including the steps of: producing crushed edible plants or edible animal/plants; culturing a liquid mixture of grains, saccharides, filamentous fungi, and yeast for 24 to 36 hours to produce a mixed microbial broth; inoculating the edible plants or edible animal/plants with the mixed microbial broth, and firstly fermenting the edible plants or edible animal/plants for 3 to 8 days to produce first fermented edible plants or edible animal/plants; and inoculating the first fermented edible plants or edible animal/plants with bacteria, and secondly fermenting the first fermented edible plants or edible animal/plants for 6 to 12 days to produce second fermented edible plants or edible animal/plants. Further, adding the fermented edible plants or edible animal/plants produced by the above-described method into foods can provide storage stability, increase bioavailability, and improve flavor.

11 Claims, 1 Drawing Sheet

(51) Int. Cl.
  *A23L 1/20* (2006.01)
  *A23L 1/212* (2006.01)
  *A23L 1/23* (2006.01)
  *A23L 1/30* (2006.01)
  *A23L 1/314* (2006.01)
  *A23L 3/3463* (2006.01)

(52) U.S. Cl.
  CPC .................. *A23L 1/212* (2013.01); *A23L 1/23* (2013.01); *A23L 1/30* (2013.01); *A23L 1/3002* (2013.01); *A23L 1/31472* (2013.01); *A23L 3/3463* (2013.01); *A23V 2002/00* (2013.01)

(56) References Cited

U.S. PATENT DOCUMENTS

| | | | | |
|---|---|---|---|---|
| 2008/0299606 | A1* | 12/2008 | Pompejus | C12P 13/08 435/67 |
| 2009/0053342 | A1* | 2/2009 | Streekstra | A23D 9/00 424/780 |
| 2009/0064567 | A1* | 3/2009 | Lippmeier | C10L 1/02 44/308 |

FOREIGN PATENT DOCUMENTS

| | | | |
|---|---|---|---|
| JP | 59-162870 | A | 9/1984 |
| JP | 60-066971 | A | 4/1985 |
| JP | 60-192584 | A | 10/1985 |
| JP | 01-104155 | A | 4/1989 |
| JP | 02-057172 | A | 2/1990 |
| JP | 02-154677 | A | 6/1990 |
| JP | 10-117722 | A | 5/1998 |
| JP | 2001-238593 | A | 9/2001 |
| JP | 2005-102598 | A | 4/2005 |
| JP | 2006-180868 | A | 7/2006 |
| JP | 2006-238857 | A | 9/2006 |
| JP | 2008-067680 | A | 3/2008 |
| JP | 2008-125469 | A | 6/2008 |
| JP | 2008183004 | A * | 8/2008 |

OTHER PUBLICATIONS

Japanese Office Action issued in Japanese Patent Appln. No. 2011-521991 on Nov. 6, 2012 along with English translation, 10 pages.

* cited by examiner

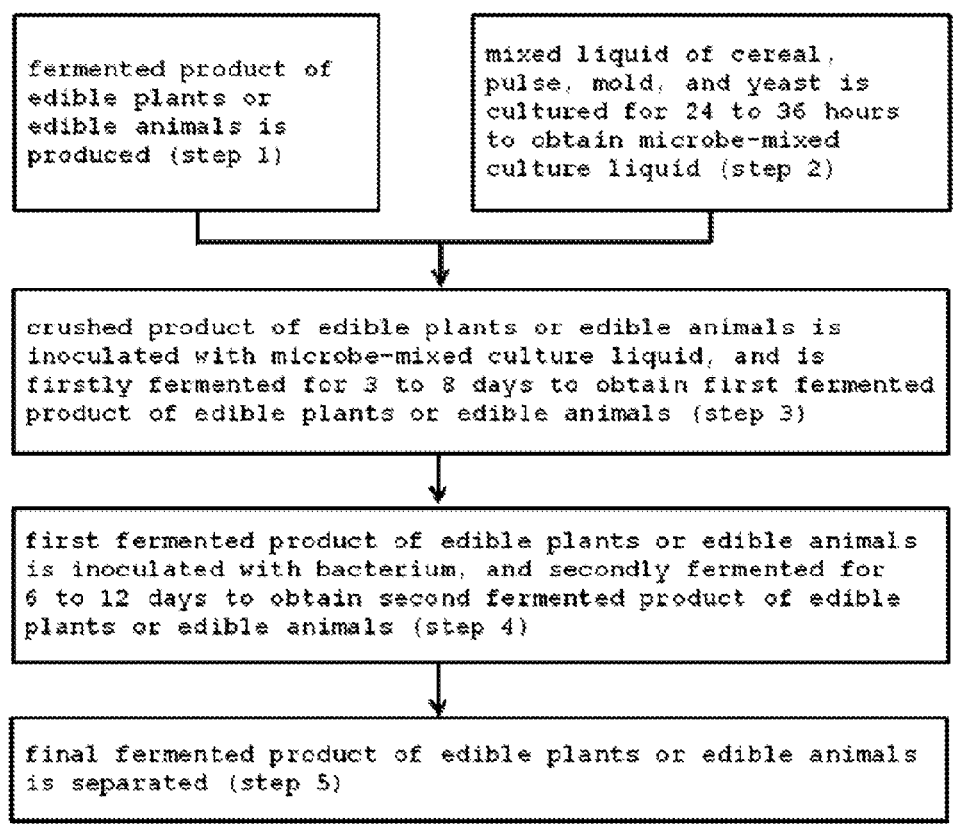

METHOD FOR PRODUCING FERMENTED EDIBLE PLANTS OR EDIBLE ANIMAL/PLANTS, FERMENTED EDIBLE PLANTS OR EDIBLE ANIMAL/PLANTS PRODUCED BY SAME, AND FOODS CONTAINING SAME

CROSS REFERENCE TO RELATED APPLICATIONS

This application is a 35 U.S.C. §371 National Phase Entry Application from PCT/KR2009/002372, filed May 6, 2009, and designating the United States, which claims priority under 35 U.S.C. §119 to Korean Patent Application No. 10-2008-0084968 filed Aug. 29, 2008, and to Korean Patent Application No. 10-2008-0084956 filed Aug. 29, 2008, which are incorporated herein in their entireties.

TECHNICAL FIELD

The present invention relates to a method of producing a fermented product of edible plants or edible animals, the fermented product produced by the method, and a food including the fermented product.

BACKGROUND ART

Fermented products of edible plants or edible animals for flavor, quality preservation, nutritional ingredient, etc. have been finally produced into various foods according to active bacteria culture liquids, and marketed worldwide. Examples of the fermented products include a fermented vegetable product such as sauerkraut produced by cabbage, and pickles produced by cucumber, a fermented seed product such as coffee or cocoa beans, fermented fruit juice, or the like. The existence of deteriorating organic substances and pathogens within a food is very problematic for the food processing industry and consumers.

A food pathogen has been a cause of food poisoning, and the resulting food poisoning has sometimes led to serious disease and death. Furthermore, the existence of pathogenic organic substances within a food has caused recalls of many products, damage to products, and a significant discredit to a food industry. Thus, in order to solve these problems, much research has been conducted.

For a long time, human beings have experimentally used about 80 kinds of useful aerobic or anaerobic microbes, including yeast, *lactobacillus*, mold, photosynthetic bacteria, actinomyces, for fermented foods. Fermentation products made from the coexistence and coprosperity between the aerobic microbes and the anaerobic microbes have been known to have an antioxidant activity and an inhibiting property on noxious substance generation.

Especially, from among these useful microbes related to fermentation, photosynthetic bacterium is one of the first life-forms which have existed on earth for up to about 3.5 billion years. It absorbs inorganic matter (such as carbon dioxide, hydrogen, methane, etc.) which had covered the ancient earth, synthesizes organic compounds, and generates oxygen. It is known that photosynthetic bacterium is the oldest microbe, is helpful to both aerobic and anaerobic microbes, and performs an important role in co-existence with heterotrophic bacteria while fixing nitrogen.

Mold is a fungus which is easily seen by people, and produces a large mount of hyphae and spores unlike yeast. Mold includes a noxious mold and a useful mold, such as *Aspergillus niger*. When existing with yeast or bacteria, it performs a role of producing various physiologically active substances (such as amino acid, polysaccharide, etc.) like yeast, and also helping the yeast to proliferate.

Yeast is the mother-body of fermentation, and is necessary for brewage and baking. It was found by Antony van Leeuwenhoek (1632~1723, Netherlands) in the 17$^{th}$ century, and surprised the world. Also, it is a kind of mold in microbe classification, and is a microbe necessary to human's living, which exists in sugar-abundant areas such as the nectar of flowers, the surface of fruits, and produces physiologically active substances such as amino acid, polysaccharide, etc.

At present, it is known that there exist about 5,000 kinds of actionomycetes, and ⅔ or more of these actionomycetes produce *Streptomyces*. The name "actinomycete" was given because it has a shape of filaments extending in all directions. Multiple actinomycetes exist in soil, and produce physiologically active substances such as antibiotic substances.

Also, *lactobacillus* is a kind of bacteria in classification, and performs a role of changing sugar to lactic acid. It has a characteristic in that it survives relatively well together with other microbes. *Lactobacillus* was first found by Pasteur in 1857, and has been found to be a microbe helpful to human's health. Furthermore, it is known to have various functions, such as antiflatulence, immunity improvement, antitumor, cholesterol inhibition, blood pressure control, and produce antioxidant substances.

However, microbes which have been conventionally used for producing fermented products of edible plants or edible animals have a problem in that the production unit cost is increased due to a long fermentation period. Furthermore, in a process-completed food, the food deterioration and the growth of a pathogenic microbe, caused by the contamination of various bacteria, reduces storage stability and results in a decrease in the flavor or bioavailability.

DISCLOSURE

Technical Problem

Accordingly, the present invention has been made to solve the above-mentioned problems occurring in the prior art, and the present invention provides a method of producing a fermented product of edible plants or edible animals, which can reduce a fermentation period, and inhibit the food deterioration and the growth of a pathogenic microbe.

Also, the present invention provides a fermented product of edible plants or edible animals, and a food including the same, in which the flavor and bioavailability are improved.

Technical Solution

In accordance with an aspect of the present invention, there is provided a method of producing a fermented product of edible plants or edible animals, the method including the steps of: producing a crushed product of the edible plants or the edible animals by crushing at least one edible plant or animal selected from the group including vegetables, fruits, potatoes, nuts, mushrooms, crude drugs, seaweeds, cereals, pulse, oil plants, meats, fishes, shellfishes, crustaceas, mollusks, echinoderms or notochords, and eggs; producing a microbe-mixed culture liquid by mixing a cereal, a saccharide, a mold, and a yeast with first sterilized purified water, culturing the resultant mixture at 25 to 30° C. for 24 to 36 hours, and mixing the cultured mixture with second sterilized purified water; obtaining a first fermented product of the edible plants or the edible animals by inoculating the crushed product of the edible plants or the edible animals with the microbe-mixed culture liquid, and firstly fermenting the resultant product at 25 to 37° C. for 3 to 8 days; and obtaining a second fermented product of the edible plants or the edible animals by inoculating the first fermented product of the edible plants or the edible animals with a bacterium in an amount of 0.5 to 1.5% with respect to weight of the first fermented product of the edible plants or the edible animals, and secondly fermenting the resultant product at 30 to 40° C. for 6 to 12 days, wherein the cereal, the saccharide, the mold, the yeast, the first sterilized purified water, and the second sterilized purified water are used in amounts of 5 to 10%, 0.5 to 2%, 0.5 to 1.5%, 0.5 to 1.5%, 5 to 10%, and 30 to 50%, respectively, with respect to weight of the crushed product of the edible plants.

The method may further include at least one from among the steps of: compressing or centrifuging, and filtrating the second fermented product of the edible plants or the edible animals to separate a liquid content from a solid content; sterilizing the liquid content at 80 to 85° C. for 10 to 30 minutes to obtain a liquid-type final fermented product of the edible plants or the edible animals; compression-concentrating the liquid content to obtain an extract-type final fermented product of the edible plants or the edible animals, or spray-drying the liquid content to obtain an extract powder-type final fermented product of the edible plants or the edible animals; and freeze-drying or hot-wind drying the solid content to obtain a powder-type final fermented product of the edible plants or the edible animals.

The method may further include the step of adding the final fermented product of the edible plants or the edible animals with at least one selected from the group including vitamins, amino acids, minerals, nutritional sources and dietary fibers, and at least one selected from the group including an acidifier, a sweetener, a flavoring agent, and natural fruit juice to obtain a food in a form of powder, granules, tablets, capsules, jelly, cream, pap or drink.

Herein, the vitamins may include at least one selected from the group including vitamins A, $B_1$, $B_2$, $B_6$, $B_{12}$, C, $D_2$, $D_3$, E, K, and folic acid.

The amino acids may include at least one selected from the group including histidine, isoleucine, leucine, lysine, methionine, valine, cystine, tryptophane, threonine, phenylalanine and tyrosine.

The minerals may include at least one selected from the group including germanium, copper, magnesium, manganese, molybdenum, selenium, zinc, iodine, iron, potassium, calcium, and chromium.

The dietary fibers may include at least one selected from the group including plantago seed husk, cellulose, hemicellulose, crystalline cellulose, lignin, pectin, alginic acid, polymannuronic acid, guar gum, Arabic gum, arabinogalactan, glucomannan, inulin, levan, polydextrose, and indigestible maltodextrin.

The nutritional sources may include honey or royal jelly. The acidifier may be at least one selected from the group including citric acid, DL-malic acid, and succinic acid.

The sweetener may be at least one selected from the group including isomerized (high fructose), aspartame, stevioside, D-sorbitol, glycyrrhizic acid salt, and white sugar.

The flavoring agent may be at least one selected from the group including mixed-fruit flavor, apple flavor, yogurt flavor, banana flavor, apricot flavor, drink flavor, and lemon flavor. Also, the natural fruit juice may be at least one selected from the group including an apple, a pear, a pineapple, a mandarin, a peach, a guava, an apricot, a strawberry, a lemon, a plum, and a melon.

According to another aspect of the present invention, there is provided a fermented product of edible plants or edible animals, manufactured by the above described method. Also, the present invention provides various foods including the fermented product, such as a nutritional supplementary food, a functional food, a health food or a tea.

Advantageous Effects

According to the producing method of the present invention, a microbe-mixed culture liquid of a mold and a yeast is separately cultured, and inoculated to a crushed product, followed by first fermentation. Herein, since the mold and the yeast are independently and efficiently cultured in the microbe-mixed culture liquid, the fermentation period of the edible plants or edible animals can be effectively reduced. Also, the microbe-mixed culture liquid of the mold and the yeast reduces aerobic microbes and increases anaerobic microbes so as to effectively inhibit the invasion or proliferation of various bacteria (pathogenic microbes) causing food deterioration. Also, the use of the microbe-mixed culture liquid facilitates the production of pectinase and tannase (breakdown enzymes of fruit skin, that is, pectic substances and tannin), and activates these enzymes, thereby improving cleanliness and flavor of the fermented product, and increasing bioavailability.

Especially, when the crushed pieces of the edible plants or edible animals are beans, and are inoculated with the microbe-mixed culture liquid including the *Aspergillus* cultured therein and firstly fermented, a large amount of glyceollin is produced. The glyceollin inhibits the growth of cancel cells (breast cancer, and ovarian cancer), and thereby prevents breast cancer, and ovarian cancer. Thus, glyceollin shows a significant effect as an anti-estrogen agent. Also, in this case, Prolylendoprotease (PEP), which is an enzyme capable of inhibiting gluten-sensitive enteropathy caused by the intake of white bread or fast food, is produced in a large amount. This enzyme is not broken down by stomach acid, and increases the digestion speed of glutenins and gliadinsin in the white bread.

Furthermore, when the first fermented product of the edible plants or the edible animals is inoculated with bacteria and secondly fermented, fermentation products of bacteria, that is, lactic acid, nitric acid, alcohol, etc. are produced in the second fermented product of the edible plants or edible animals. These fermentation products effectively inhibit the proliferation of harmful bacteria within the second fermented product of the edible plants or edible animals and provides flavor, thereby producing aromatic components such as diacetyl or acetonin. Also, the fermentation products provide characteristic flavor by decomposing a part of a protein of substances included within the second fermented product of the edible plants or edible animals, into peptide or amino acid. This improves the flavor of the fermented product of the edible plants or edible animals, obtained by the method according to the present invention.

Also, in the fermented product of the edible plants or edible animals, amylase, protease, and lipase are produced, which improves digestion/absorption and bioavailability of the product. Also, the fermented product of the edible plants or edible animals has enhanced substances, such as various kinds of organic acids, carbohydrates, vitamins, minerals, amino acids, unsaturated fatty acids, and dietary fibers.

Accordingly, the fermented product of the edible plants or the edible animals, according to the present invention, may be manufactured in the form of a food composition. The food composition may have various forms, such as a functional food, a nutritional supplementary food, a health food, a tea, etc. The addition of the fermented product of the edible plants or the edible animals according to the present invention, to a food, improves the taste and flavor of the food, facilitates digestion/absorption, and enhances various nutrients.

BRIEF DESCRIPTION OF THE DRAWINGS

The foregoing and other objects, features and advantages of the present invention will become more apparent from the following detailed description when taken in conjunction with the accompanying drawings in which:

FIG. 1 is a flow chart sequentially illustrating the process of producing a fermented product of edible plants or edible animals, according to a preferred exemplary embodiment of the present invention.

BEST MODE

Mode for Invention

Hereinafter, preferred embodiments of the present invention will be described in detail with reference to a drawing. However, the present invention may be embodied in many different forms and should not be construed as limited to the embodiments set forth herein. Rather, these embodiments are provided so that this disclosure will be thorough and complete, and will fully convey the scope of the invention to those skilled in the art.

FIG. 1 is a flow chart sequentially illustrating a process of producing fermentation of edible plants or edible animals, according to a preferred exemplary embodiment of the present invention.

Hereinafter, a method of producing fermentation of edible plants or edible animals, according to the present invention, will be described with reference to FIG. 1.

[Step 1: production of Crushed Pieces of Edible Plants or Edible Animals]

The raw material of the fermentation of edible plants or edible animals, according to the present invention, may be at least one selected from the group including vegetables, fruits, potatoes, nuts, mushrooms, crude drugs, seaweeds, cereals, pulse, oil plants, meats, fishes, shellfishes, crustaceas, mollusks, echinoderms or notochords, and eggs;

(1) vegetables: leafy and stem vegetables (leaf mustard, chard, cauliflower, angelica keiskei, dropwort, Chinese cabbage, broccoli, celery, spinach, crown daisy, asparagus, curled mallow, cabbage, lettuce, kale, spring onion, parsley, bok choy, chicory, etc.), root vegetables (radish, turnip, carrot, onion, lotus root, burdock, taro, yam, garlic, etc.), garden fruits (cucumber, squash, tomato, eggplant, strawberry, oriental melon, melon, watermelon, pumpkin, paprika, pimento, red pepper, etc.), (2) fruits: persimmon, citrus fruits (tangerine, orange, grapefruit, lemon, citron, mandarin orange, etc.), fruit of actinidia arguta, jujube, mango, papaya, fig, banana, pear, cherrybob, blueberry, peach, apple, zizyphus jujube var. spinosa, apricot, pomegranate, avocado, cherry, mulberry, plum, kiwi, cherry, coconut, longan, etc.

(3) potatoes: potato, sweet potato, cassava, yam, tapioca, etc.

(4) nuts: peanut, almond, chestnut, walnut, pine nut, gingko nut, acorn, cacao, etc.

(5) mushrooms: coriolus versicolor, oyster mushroom, cordyceps militaris, black mushroom, umbilicaria ediblea, tricholoma matsutake, clavaria, phellinus linteus, agaricus, button mushroom, Ling Chiu mushroom, coriolus versicolor, winter mushroom, oak mushroom, etc.

(6) crude drugs: Puerariae Radix., Puerariae Flos, Chrysanthemi Flos, Euphorbiae kansui Radix, Euryale ferox Salisbury, Glycyrrhizae Radix, Ostericum Koreanum, Zingiberis siccatum Rhizoma, Euryale Semen, Platycodi Radix, Sinapis Semen, Cassiae Semen, Galli Stomachichum Corium, Cassiae Cortex, Sophorae Radix, Oryza sativa (rice), Agastache rugosa, Trichosanthes kirilowii, Sophorae flos, Lycii Fructus, Chrisanthemi sibirici Herba, Testudins Plastrum, Psidium guajava, Lonicerae Flos, Raphani Semen, Phragmitis Rhizoma, antler, hartshorn, aloe, Echinopsis Radix, Salviae Radix, Angelica Sinensis Radix, Codonopsis pilosulae radix, Arecae Pericarpium, Rhei Rhizoma, Illicium vernum, euphorbiaceae plants, Persicae Semen, Araliae cordatae Radix, Benincasae Semen, Malvae Semen, Eucomiae Cortex, Juncus decipiens, Cannabis Semen, mate, Ephedrae Herba, Viticis Fructus, Hordei Fructus Germinatus, Liriopis Tuber, Gossypii Semen, Chaenomelis Fructus, Moutan Cortex Radicis, Akebiae Caulis, Saussureae Radix, Myrrha, Mentha Herba, Pinelliae Tuber, Sinomenium acutum, Ledebouriellae Radix, Bombycis corpus, Amomi Cardamomi Fructus, Thujae Semen, Angelicae Dahuricae Radix, Atractylodis Rhizome Alba, Trionycis Carapax, Psoraleae Semen, Hoelen, Rubi Fructus, Zedoariae Rhizoma, Eriobotriae Follum, Arecae Pericarpium, Adenophorae Radix, Torilidis Fructus, Amomi Semen, saffron, Crataegi fructus, Corni Fructus, Zizyphi Spinosi Semen, Zanthoxyli Fructus, Scirpi Rhizoma, Loranthi Ramulus, Mori Folium, Mantidis ootheca, ginger, Cassia occidentalis, Dendrobii Herba, Acori Graminei Rhizoma, Asiasari Radix, Cardamomi Fructus, Caesalpiniae Lignum, Perillae Semen, Dipsacus asper, Pini Pollen, Cynomorii Herba, Cimicifugae Rhizoma, Bupleuri Radix, Massa Medicata Fermentata, Magnoliae Flos, Asini Gelatinum, Alpiniae Rhizoma, Artemisiae Argyi Folium, Ligustri Fructus, Nelumbinis Semen, Forsythiae Fructus, Rosae Fructus, Acanthopanacis Cortex, Scolopendra, Aconitum carmichaeli Debeaux, Trogopterorum Faeces, Mume Fructus, Schizandrae Fructus, Evodiae Fructus, Linderae Radix, Otariae testis et Penis, Orostachys Herba, Fossilia ossis Mastodi, Borneolum, Fel bovinum, Arctii Semen, Achuranthis Radix, Curcumae longae Rhizoma, Polygalae Radix, Clematidis Radix, Polygonati odorati Rhizoma, ulmus, Olibanum, Myristicae Semen, Cistanchis Herba, Epimendii Herba, Alpiniae Semen, Lonicerae Folium, Ginseng Radix, Artemisiae Messerschmidtiana Herba, Santalini Lignum Rubrum, Asteris Radix, Hominis Placenta, Paeoniae Radix, Bombycis Excrementum, jasmine, Polyporus, scorpio, peucedani radix, bambusae caulis in taeniam, caryophylli flos, houttuyniae herba, aurantii fructus, hoveniae lignum, anemarrhenae rhizoma, ponciri fructus, sanguisorbae radix, rhemaniae radix, aurantii nobilis pericarpium, tribuli fructus, green tea, plantaginis semen, xanthii fructus, atractylodis rhizoma, arisaematis rhizoma, cnidii rhizoma, gastrodiae rhizoma, asparagi tuber, zanthoxyli pericarpium, aurantii immatri pericarpium, alpiniae katsumadaii semen, biotae orientalis folium, aquilariae resinatum lignum, gardenia fructus, chamomile, coffee, alismatis rhizoma, cuscutae semen, morindae officinalis radix, tiglii semen, fritillariae bulbus, taraxaci herba, piperis longi fructus, aconiti tuber, prunellae spica, polygoni multiflori radix, shell powder, kalopanacis cortex, armeniacae semen, cyperi rhizoma, elscholtziae herba, scrophulariae radix, nepetae spica, scutellariae radix, astragali radix, phellodendri cortex, coptidis rhizoma, polygonati rhizoma, hop, cartami flos, machili cortex, pepper, Siegesbeckia glabrescens, foeuicuiculi fructus, pharbitidis semen, etc.

(7) seaweeds: sea lettuce, ecklonia stolonifera, laver, sea string, kelp, gigartina tenella, pelvetia siliquosa, seaweed fulvescens, sea mustard, spirulina, agar, sea staghorn, chlorella, seaweed fusiforme, enteromorpha, slander glasswort, etc.

(8) cereals: rice, glutinous rice, unpolished rice, black rice, rice bran, barley, wheat, rye, oat, millet, sorghum, corn, buck wheat, adlay, panicum miliaceum, etc.

(9) pulse: soybean, red bean, mung bean, kidney bean, pea, cowpea, broad bean, butter bean, chickpea, green bean, black bean, lentil, etc.

(10) oil plants: sesame, green perilla, black sesame, sunflower seed, olive, evening primrose seed, cottonseed, rape seed (canola seed), palm, safflower seed, etc.

(11) meats: venison, chevon, mutton, beef, ostrich, badger, crocodile, seal, phoca groenlandica, whale, edible frog, edible snail, edible terrapin, etc.

(12) fishes: snakehead fish, codfish, sea bream, common eel, loach, croaker, shark, carp, eel, etc.

(13) shellfishes: oyster, sea mussel, ark shell, corbicula, turban, clam, ear shell, short-necked clam, etc.

(14) crustaceas: shrimp, crab, lobster, crawfish, small crab, krill, etc.

(15) mollusks: octopus, squid, common octopus, edible cuttle fish, urechis unicinctus, sea hare, beka squid, octopus ocellatus, jellyfish, etc.

(16) echinoderms or notochords: sea urchin, sea cucumber, sea squirt, warty sea squirt, etc.

(17) eggs: hen's egg, duck's egg, common quail's egg, etc.

From among the above mentioned edible plants or edible animals used in the present invention, one or more kinds are selected, and are washed by water-tank immersion or rotary-spray, followed by spin-drying. Then, a crusher is used to roughly grind or pulverize the washed edible plants or animals. The crushed pieces of the edible plants or animals are transferred to a fermenting tank. The crushed pieces of the two or more kinds of the edible plants or animals may be mixed in various ratios before being transferred to the fermenting tank. Also, the above mentioned plants and animals may be mixed in various ratios through this process.

[Step 2: Production of a Microbe-Mixed Culture Liquid Through Culture of a Mold/Yeast Mixed Liquid]

The microbe-mixed culture liquid to be added to a fermented product of the edible plants or edible animals, according to the present invention, is produced by adding a mold, yeast, and saccharide to steam-sterilized cereals. Herein, as required, 5 to 10% of sterilized purified water may be added. The resultant mixture is cultured at 25 to 35° C. for 24 to 36 hours. Otherwise, cereals are inoculated with a mold and cultured for 24 hours, and then are further inoculated with saccharide and yeast and cultured for 12 hours. Herein, sterilized purified water is added in an amount of 30 to 50% with respect to the weight of the crushed pieces of the edible plants or edible animals. The mold/yeast microbe mixed culture liquid obtained through the culture (hereinafter, referred to as a microbe-mixed culture liquid) is used for first fermentation.

The cereal that may be used in the present invention has to be edible, and may be one or any combination selected from the group including rice, glutinous rice, oat, adlay, black rice, unpolished rice, rice bran, barley, wheat, wheat bran, and bean. The cereal may be added in an amount of 5 to 10% with respect to the weight of the crushed pieces of the edible plants or edible animals in the step 1, in the production of the microbe-mixed culture liquid.

The saccharide that may be used in the present invention has to be edible, and may be one or any combination selected from the group including sugar, glucose, fructose, wheat-glutens, syrups, dextrin, and oligosaccharide. The saccharide may be added in an amount of 0.5 to 2% with respect to the weight of the crushed pieces of the edible plants or edible animals in the step 1, in the production of the microbe-mixed culture liquid.

The mold that may be used in the present invention may be one or any combination selected from the group including *Aspergillus oryzae, Aspergillus niger*, and *Aspergillus sojae*. The mold may be added in an amount of 0.5 to 1.5% with respect to the weight of the crushed pieces of the edible plants or edible animals in the step 1, in the production of the microbe-mixed culture liquid.

The yeast that may be used in the present invention may be one or combination of *Saccharomyces cerevisiae*, and *Saccharomyces ellipsoideus*. The yeast may be added in an amount of 0.5 to 1.5% with respect to the weight of the crushed pieces of the edible plants or edible animals in the step 1, in the production of the microbe-mixed culture liquid.

There is no limitation in a culture medium that may be used in the present invention, as long as it contains cereals and saccharide to proliferate mold and yeast. The culture medium is generally in a liquid state where water is added with cereals and saccharide, but may be in a solid state.

[Step 3: Production of a First Fermented Product of Edible Plants or Edible Animals Through Inoculation of the Microbe-Mixed Culture Liquid to the Crushed Pieces of the Edible Plants or Edible Animals, and the First Fermentation]

The crushed pieces of the edible plants or edible animals in step 1 are inoculated with the microbe-mixed culture liquid in step 2, followed by stirring. After the materials are uniformly mixed, the resultant mixture is firstly fermented at 25 to 37° C. for 3 to 8 days to provide a first fermented product of the edible plants or edible animals. In the fermentation using a microbe, a nutritional ingredient such as starch is hydrolyzed into glucose, and the glucose is used as a nutritional source for facilitating the growth of the microbe so as to produce organic acid. This further increases the content of a useful substance and the organic acid.

In the first fermentation, the microbe-mixed culture liquid, in which the mold and the yeast were independently and efficiently cultured, is used so that the fermentation period of the edible plants or edible animals can be effectively reduced. Also, the microbe-mixed culture liquid including the mold and the yeast reduces aerobic microbes and increases anaerobic microbes so as to effectively inhibit the invasion or proliferation of various bacteria (pathogenic microbes) causing food deterioration. Also, the use of the microbe-mixed culture liquid facilitates the production of pectinase and tannase (breakdown enzymes of fruit skin, that is, pectic substances and tannin), and activates these enzymes, thereby improving cleanliness and flavor of the fermented product, and increasing bioavailability.

Especially, when the crushed pieces of the edible plants or edible animals are beans, and are inoculated with the microbe-mixed culture liquid including the *Aspergillus* cultured therein and firstly fermented, a large amount of glyceollin is produced. The glyceollin inhibits the growth of cancel cells (breast cancer, and ovarian cancer), and thereby prevents breast cancer, and ovarian cancer. Thus, glyceollin shows a significant effect as an anti-estrogen agent. Also, in this case, Prolylendoprotease (PEP), which is an enzyme capable of inhibiting gluten-sensitive enteropathy caused by the intake of white bread or fast food, is produced in a large amount. This enzyme is not broken down by stomach acid, and increases the digestion speed of glutenins and gliadinsin in the white bread.

[Step 4: Production of a Second Fermented Product of Edible Plants or Edible Animals Through Inoculation of Bacteria to the First Fermented Product of the Edible Plants or Edible Animals, and Second Fermentation]

The first fermented product of the edible plants or edible animals in step 3 is inoculated with bacteria including a *lactobacillus* in an amount of 0.5 to 1.5% with respect to the weight of the first fermented product of the edible plants or edible animals, followed by stirring. After the materials are uniformly mixed, the resultant mixture is secondly fermented at 30 to 40° C. for 6 to 12 days to provide a second fermented product of the edible plants or edible animals.

The second fermentation using bacteria such as a *lactobacillus* is to allow a finally fermented product to contain various kinds of useful substances produced by the *lactobacillus* as well as organic acid within the first fermented product of the edible plants or edible animals. The bacteria that may be used in the fermented product of the edible plants or edible animals according to the present invention may be one or any combination selected from the group including *Leuconostoc mensenteroides, Lactobacillus acidophillus, Lactobacillus plantarum, Lactobacillus brevis, Bacillus subtilis, Bacillus licheniformis,* and *Bacillus megaterium.*

As a result of the second fermentation, fermentation products of bacteria (such as a *lactobacillus*), that is, lactic acid, nitric acid, alcohol, etc. are produced in the second fermented product of the edible plants or edible animals. These fermentation products effectively inhibit the proliferation of harmful bacteria within the second fermented product of the edible plants or edible animals and provides flavor, thereby producing aromatic components such as diacetyl or acetonin. Also, the fermentation products provide characteristic flavor by decomposing a part of a protein of substances included within the second fermented product of the edible plants or edible animals, into peptide or amino acid. This improves the flavor of the fermented product of the edible plants or edible animals, obtained by the method according to the present invention.

Also, in the fermented product of the edible plants or edible animals, amylase, protease, and lipase are produced, which improves digestion/absorption and bioavailability of the product. Also, the fermented product of the edible plants or edible animals has enhanced substances, such as various kinds of organic acids, carbohydrates, vitamins, minerals, amino acids, unsaturated fatty acids, and dietary fibers.

[Step 5: Production of a Liquid or Solid Fermented Product of the Edible Plants or Edible Animals Through Compression or Centrifuge of the Second Fermented Product of the Edible Plants or Edible Animals]

The second fermented product of the edible plants or edible animals, obtained through the second fermentation in step 4, is subjected to compression or centrifuge, and filtration, so as to separate a liquid content from a solid content. The liquid content and the solid content may be utilized as described below:

(1) the liquid content may be used as a liquid-fermented product of the edible plants or edible animals through sterilization at 80 to 85° C. for 10 to 30 minutes;

(2) the liquid content may be decompression-concentrated so as to be made into an extract of the fermented product of the edible plants or edible animals, or may be spray-dried so as to be made into extract powder of the fermented product of the edible plants or edible animals; and (3) the solid content may be freeze-dried or hot-wind dried, and crushed so as to be made into powder type of the fermented product of the edible plants or edible animals.

Through these processes, the fermented product of the edible plants or edible animals can be manufactured.

Example 1

Manufacture of a Fermented Product of Edible Plants-1

20 kg of grapes, 10 kg of strawberries, 10 kg of oriental melons, 10 kg of dropworts, 10 kg of broccolis, 10 kg of crown daises, 10 kg of kales, 5 kg of radishes, 2 kg of cucumbers, 2 kg of pears, 2 kg of balloonflowers, 1 kg of kelps, 1 kg of slander glassworts, 2 kg of yams, 1 kg of garlics, 1 kg of oak mushrooms, 1 kg of schizandra, 1 kg of mate, and 1 kg of red peppers were put in a water immersion tank, washed by clean water, and dehydrated. Then, the dehydrated materials were cut-crushed into a size of 5 to 10 cm or pulverized to provide a crushed product of edible plants, and the obtained crushed product was placed in a fermentation tank.

Before the above described process, 5 kg of rice bran and 5 kg of wheat bran were mixed with each other and the mixture was steam-sterilized and cooled to room temperature. Then, 0.7 kg of unrefined sugar, 0.4 kg of *Aspergillus niger*, 0.4 kg of *Aspergillus oryzae*, and 0.8 kg of *Saccharomyces cerevisiae* were added thereto. Also, sterilized purified water may be added thereto. Then, after being cultured at 25 to 35° C. for 36 hours, 40 kg of sterilized purified water was added so as to provide a microbe-mixed culture liquid A.

The microbe-mixed culture liquid A was transferred to the fermentation tank containing the crushed product of the edible plants, and mixed with the crushed product. The resultant mixture was firstly fermented at 25° C. for 8 days to provide a first fermented product of the edible plants. Then, the first fermented product of the edible plants was inoculated with 1.1 kg of *Leuconostoc mensenteroides* (*lactobacillus*), and was secondly cultured at 33 to 35° C. for 10 days to provide a second fermented product of the edible plants. For the first and second fermentation cultures, as required, sterilized purified water may be added. The second fermented product of the edible plants was compressed or centrifuged, and filtrated so as to separate a liquid content from a solid content. The liquid content was sterilized at 85° C. for 15 minutes, and added with a small amount of vitamins and a sweetener to provide a liquid-type fermented product of the edible plants.

Example 2

Manufacture of a Fermented Product of Edible Plants-2

20 kg of adlay, 15 kg of yam, 8 kg of squash, 8 kg of strawberry, 8 kg of paprika, 2 kg of angelica keiskei, 2 kg of slander glasswort, 4 kg of asparagus, 4 kg of lotus root, 4 kg of apple, 4 kg of potato, 4 kg of kidney beans, 2 kg of ginseng, 2 kg of chestnut, 1 kg of red pepper, 1 kg of cucumber, 2 kg of garlics, 2 kg of radishes, 2 kg of astragali radix, 2 kg of oyster mushrooms, 1.5 kg of mugwort, 1 kg of pine needles, 1 kg of ginger, 1 kg of lemon, and 0.5 kg of green perilla were placed in a water immersion tank, washed by clean water, and dehydrated. Then, the dehydrated materials were cut-crushed into a size of 5 to 10 cm or pulverized to provide a crushed product of edible plants, and the obtained crushed product was placed in a fermentation tank.

Before the above described process, 5 kg of unpolished rice, and 5 kg of barley were washed, and mixed with each other, and the mixture was steam-sterilized and cooled to room temperature. Then, 0.5 kg of *Aspergillus oryzae* and 0.5 kg of *Aspergillus sojae* were mixed and inoculated thereto. Herein, as required, sterilized purified water may be added to control humidity. Then, after first culture at 25 to 35° C. for 24 hours, the firstly cultured mixture was added with 3 kg of sterilized purified water, 0.4 kg of glucose, 0.7 kg of *Saccharomyces cerevisiae*, and 0.4 kg of *Saccharomyces ellipsoideus*, and secondly cultured at 25 to 30° C. for 12 hours. Then, 30 kg of sterilized purified water was added to the secondly cultured mixture so as to provide a microbe-mixed culture liquid B.

The microbe-mixed culture liquid B was transferred to the fermentation tank containing the crushed product of the edible plants, and mixed with the crushed product. The resultant mixture was firstly fermented at 25 to 26° C. for 8 days to provide a first fermented product of the edible plants. Then, the first fermented product of the edible plants was inoculated with 1.2 kg of a mixture of *Leuconostoc mensenteroides* and *Lactobacillus plantarum* (*lactobacillus*), and was secondly cultured at 33 to 35° C. for 10 days to provide a second fermented product of the edible plants. For the first and second fermentation cultures, as required, sterilized purified water may be added.

The second fermented product of the edible plants was compressed or centrifuged so as to separate a liquid content from a solid content. The solid content was hot-wind dried, crushed into powder with 140 to 160 meshes, and added with dietary fibers, seaweed calcium, and vitamins to provide a powder-type fermented product of the edible plants.

Example 3

Manufacture of a Fermented Product of Edible Plants-3

23 kg of rice bran, 20 kg of unpolished rice, 20 kg of barley, 15 kg of adlay, 10 kg of soybeans, 5 kg of buckwheat, 3 kg of carrots, 3 kg of squash, 3 kg of sweet potato, 2 kg of tomatoes, 2 kg of broccoli, 2 kg of paprika, and 2 kg of balloonflowers were placed in a water immersion tank, washed by clean water, and dehydrated. Then, the dehydrated materials were cut-crushed into a size of 5 to 10 cm or pulverized to provide a crushed product of edible plants, and the obtained crushed product was steam-sterilized, and placed in a fermentation tank.

10 kg of the microbe-mixed culture liquid A and 10 kg of the microbe-mixed culture liquid B, fermented and cultured in Examples 1 and 2, were mixed with each other. Then, the mixture was transferred to the fermentation tank containing the crushed product of the edible plants, and mixed with the crushed product. The resultant mixture was firstly fermented at 25 to 27° C. for 8 days to provide a first fermented product of the edible plants. Then, the first fermented product of the edible plants was inoculated with 1.2 kg of a mixture of *Leuconostoc mensenteroides* and *Lactobacillus brevis* (*lactobacillus*), and was secondly cultured at 34 to 36° C. for 10 days to provide a second fermented product of the edible plants. For the first and second fermentation cultures, as required, sterilized purified water may be added.

The second fermented product of the edible plants was compressed or centrifuged, and filtrated, so as to separate a liquid content from a solid content. The liquid content was decompression-concentrated to be made into an extract of the fermented product. Then, the extract was dried, crushed into powder with 140 to 160 meshes, and added with dietary fibers, and an acidifier to provide an extract powder-type fermented product of the edible plants.

Example 4

Manufacture of a Fermented Product of Edible Animals and Plants-1

10 kg of antlers, 10 kg of seal, 10 kg of edible terrapin, 10 kg of cauliflower mushrooms, 10 kg of agaricus, 10 kg of barley, 10 kg of soybeans, 10 kg of rice, 10 kg of rice bran, 5 kg of ginseng, and 5 kg of ear shell were placed in a water immersion tank, washed by clean water, and dehydrated. Then, the dehydrated materials were cut-crushed into a size of 5 to 10 cm or pulverized, and steam-sterilized to provide a crushed product of edible animals and plants, and the obtained crushed product was placed in a fermentation tank.

10 kg of the microbe-mixed culture liquid A, fermented and cultured in Example 1, was transferred to the fermentation tank containing the crushed product of the edible animals/plants, and mixed with the crushed product. The resultant mixture was firstly fermented at 35° C. for 5 days to provide a first fermented product of the edible animals/plants. Then, the first fermented product of the edible animals/plants was inoculated with 0.6 kg of *Bacillus subtillus* and 0.6 kg of *Lactobacillus acidophillus* (bacteria), and was secondly cultured at 34 to 37° C. for 5 days to provide a second fermented product of the edible animals/plants. For the first and second fermentation cultures, as required, sterilized purified water may be added. The second fermented product of the edible animals/plants was compressed or centrifuged, and filtrated so as to separate a liquid content from a solid content. The liquid content was sterilized at 85° C. for 15 minutes, and added with a small amount of vitamins and a sweetener to provide a liquid-type fermented product of the edible animals/plants.

Example 5

Manufacture of a Fermented Product of Edible Animals and Plants-2

20 kg of antlers, 20 kg of rice bran, 20 kg of barley, 10 kg of soybeans, 10 kg of seal, 10 kg of ginseng, and 10 kg of slander glasswort were placed in a water immersion tank, washed by clean water, and dehydrated. Then, the dehydrated materials were cut-crushed into a size of 3 to 6 cm or pulverized to provide a crushed product of edible animals/plants, and the obtained crushed product was steam-sterilized, and placed in a fermentation tank.

Besides, 5 kg of cnidii rhizoma, 5 kg of Atractylodis Rhizome Alba, 5 kg of hoelen, 5 kg of Glycyrrhizae Radix, 5 kg of Rehmanniae Radix Preparat, 5 kg of Paeoniae Radix, 5 kg of Angelica Sinensis Radix, 5 kg of astragali radix, 5 kg of cinnamon, 3 kg of ginger, and 2 kg of jujube were washed by water, and placed in an extraction tank. Then, purified water was added to the tank in an amount of 4 to 10 times the weight of the raw materials to obtain an extract of the materials, and the filtrate was put in the fermentation tank.

10 kg of the microbe-mixed culture liquid A and 10 kg of the microbe-mixed culture liquid B, fermented and cultured in Examples 1 and 2, were mixed with each other. Then, the mixture was transferred to the fermentation tank containing the crushed product of the edible animals/plants, and mixed with the crushed product. The resultant mixture was firstly fermented at 34 to 36° C. for 6 days to provide a first fermented product of the edible animals/plants. Then, the first fermented product of the edible animals/plants was inoculated with 1.2 kg of a mixture of Bacillus licheniformis (0.6 kg) and Leuconostoc mensenteroides (0.6 kg) (bacteria), and was secondly cultured at 33 to 37° C. for 9 days to provide a second fermented product of the edible animals/plants. For the first and second fermentation cultures, as required, sterilized purified water may be added. The second fermented product of the edible animals/plants was compressed or centrifuged, and filtrated so as to separate a liquid content from a solid content. The liquid content and the solid content were used to manufacture liquid-type and powder-type fermented products of the edible animals/plants.

Example 6

Manufacture of a Nutritional Supplementary Food Containing a Fermented Product of Edible Plants-1

5 kg of the liquid-type fermented product of the edible plants obtained from Example 1, 1.5 kg of polydextrose (90% or more of dietary fibers), 0.32 kg of indigestible dextrin (90% or more of dietary fibers), 0.13 kg of inulin (90% or more of dietary fibers), 1.2 kg of mate extract (mate 100%, solid content 3%), 0.15 kg of garcinia cambogia peel extract powder, 0.05 kg of green tea extract powder, 0.03 kg of prune juice powder, and 91.62 kg of purified water were mixed and processed to manufacture a nutritional supplementary food.

Example 7

Manufacture of a Health Food Containing a Fermented Product of Edible Plants-2

3 kg of the powder-type fermented product of the edible plants obtained from Example 2, 57 kg of plantago seed husk powder (90% or more of dietary fibers), 3 kg of Polymannuronic acid (70% or more of dietary fibers), 23.7 kg of aloe powder, 7 kg of kelp powder, 3.5 kg of garcinia cambogia peel extract powder, 0.6 kg of stevioside, 1.1 kg of green tea extract powder, and 1.1 kg of prune juice powder were mixed and processed to manufacture a health food.

Example 8

Manufacture of a Health Food Containing a Fermented Product of Edible Animals/Plants 4 kg of extract powder-type fermented product of the edible animals/plants obtained from Example 3, 47.514 kg of cereal enzyme culture, 35 kg of isolated soy protein, 10 kg of agar powder, 1 kg of calcium carbonate, 0.75 kg of magnesium oxide, 0.063 kg of zinc oxide, 0.23 kg of vitamin $B_1$ mononitrate, 0.12 kg of pyridoxine hydrochloride, 0.12 kg of nicotine acid amide, 0.8 kg of vitamin C, 0.2 kg of calcium pantothenate, 0.2 kg of riboflavin, and 0.003 kg of folic acid were mixed and processed to manufacture a health food.

Example 9

Manufacture of a Tea Containing a Fermented Product of Edible Plants 4 kg of extract powder-type fermented product of the edible plants obtained from Example 3, 12 kg of mate extract powder, 12 kg of Cassiae Semen powder, 12 kg of Lycii Fructus powder, 12 kg of Crataegi fructus powder, 12 kg of polygoni multiflori radix powder, and 36 kg of unpolished rice powder were mixed and processed to manufacture a tea.

The food composition according to the present invention is not limited to the foods obtained from Examples 6 to 9, and may include various compositions containing a fermented product of edible plants or animals, manufactured according to the method of the present invention. Also, such food compositions may be manufactured in various forms according to a conventional method known in the art.

The invention claimed is:

1. A method of producing a fermented product of edible plants alone or edible animals, the method comprising the steps of:

producing a crushed product of the edible plants or the mixture of edible plants and edible animals by crushing at least one edible plant or a mixture of at least one edible plant and at least one edible animal selected from the group consisting of vegetables, fruits, potatoes, nuts, mushrooms, crude drugs, seaweeds, cereals, pulse, oil plants, meats, fishes, shellfishes, crustaceas, mollusks, echinoderms or notochords, and eggs;

producing a microbe-mixed culture liquid by mixing a cereal, a saccharide, at least one mold selected from the group consisting of Aspergillus oryzae, Aspergillus niger and Aspergillus sojae, and a yeast selected from Saccharomyces cerevisiae or Saccharomyces ellipsoideus with first sterilized purified water, culturing the resultant mixture at 25 to 30° C. for 24 to 36 hours, and mixing the cultured mixture with second sterilized purified water, wherein the cereal, the saccharide, the mold, the yeast, the first sterilized purified water, and the second sterilized purified water are used in amounts of 5 to 10%, 0.5 to 2%, 0.5 to 1.5%, 0.5 to 1.5%, 5 to 10%, and 30 to 50%, respectively, with respect to weight of the crushed product of the edible plants or the mixture of edible plants and edible animals;

obtaining a first fermented product of the edible plants or the mixture of edible plants and edible animals by inoculating the crushed product of the edible plants or the mixture of edible plants and edible animals with the microbe-mixed culture liquid, and firstly fermenting at 25 to 37° C. for 3 to 8 days to obtain the first fermented product;

obtaining a second fermented product of the edible plants or the mixture of edible plants and edible animals by inoculating the first fermented product of the edible plants or the mixture of edible plants and edible animals with at least one bacterium selected from the group consisting of Leuconostoc mensenteroides, Lactobacillus acidophillus, Lactobacillus plantarum, Lactobacillus brevis, Bacillus subtilis, Bacillus licheniformis and Bacillus megaterium in an amount of 0.5 to 1.5% with respect to weight of the first fermented product of the edible plants or the mixture of edible plants and edible animals, and secondly fermenting at 30 to 40° C. for 6 to 12 days to obtain the second fermented product; and compressing or centrifuging, and filtering the second fermented product of the edible plants or the mixture of edible plants and edible animals to separate a liquid content from a solid content.

2. A method of producing a fermented product of edible plants alone or a mixture of edible plants and edible animals, the method comprising the steps of:

producing a crushed product of the edible plants or the mixture of edible plants and edible animals by crushing at least one edible plant or a mixture of at least one edible plant and at least one edible animal selected from the group consisting of vegetables, fruits, potatoes, nuts, mushrooms, crude drugs, seaweeds, cereals, pulse, oil plants, meats, fishes, shellfishes, crustaceas, mollusks, echinoderms or notochords, and eggs;

sterilizing and cooling the crushed product of the edible plants or the mixture of edible plants and edible animals;

washing one or more crude drugs with water and adding purified water to the one or more crude drugs in an amount of 4 to 10 times weight of the crude drugs so as to extract a crude-drug-extracted filtrate;

producing a microbe-mixed culture liquid by mixing a cereal, a saccharide, a mold, and a yeast with first sterilized purified water, culturing the resultant mixture at 25 to 30° C. for 24 to 36 hours, and mixing the cultured mixture with second sterilized purified water, wherein the cereal, the saccharide, the mold, the yeast, the first sterilized purified water, and the second sterilized purified water are used in amounts of 5 to 10%, 0.5 to 2%, 0.5 to 1.5%, 0.5 to 1.5%, 5 to 10%, and 30 to 50%, respectively, with respect to weight of the crushed product of the edible plants or the mixture of edible plants and edible animals;

obtaining a first fermented product of the edible plants or the mixture of edible plants and edible animals by mixing the crude-drug-extracted filtrate with the crushed product of the edible plants or the mixture of edible plants and edible animals, inoculating the resultant mixture with the microbe-mixed culture liquid, and firstly fermenting at 25 to 37° C. for 3 to 8 days to obtain the first fermented product;

obtaining a second fermented product of the edible plants or the mixture of edible plants and edible animals by inoculating the first fermented product of the edible plants or the mixture of edible plants and edible animals with a bacterium in an amount of 0.5 to 1.5% with respect to weight of the first fermented product of the edible plants or the mixture of edible plants and edible animals, and secondly fermenting at 30 to 40° C. for 6 to 12 days to obtain the second fermented product; and compressing or centrifuging, and filtering the second fermented product of the edible plants or the mixture of edible plants and edible animals to separate a liquid content from a solid content, wherein the mold is at least one selected from the group including *Aspergillus oryzae, Aspergillus niger* and *Aspergillus sojae*, wherein the yeast is one of *Saccharomyces cerevisiae* or *Saccharomyces ellipsoideus*, and wherein the bacterium is at least one selected from the group including *Leuconostoc mensenteroides, Lactobacillus acidophillus, Lactobacillus plantarum, Lactobacillus brevis, Bacillus subtilis, Bacillus licheniformis* and *Bacillus megaterium*.

3. The method as claimed in claim 1, further comprising the steps of:

sterilizing the liquid content at 80 to 85° C. for 10 to 30 minutes to obtain a liquid-final fermented product of the edible plants or the mixture of edible plants and edible animals; and compression-concentrating the liquid content to obtain an extract final fermented product of the edible plants or the mixture of edible plants and edible animals, or spray-drying or freeze-drying the liquid content to obtain an extract powder-final fermented product of the edible plants or the mixture of edible plants and edible animals.

4. The method as claimed in claim 1, further comprising the step of freeze-drying or hot-wind drying the solid content to obtain a powder-type final fermented product of the edible plants or the mixture of edible plants and edible animals.

5. The method as claimed in claim 3, further comprising the step of adding the final fermented product of the edible plants or the mixture of edible plants and edible animals with at least one selected from the group consisting of vitamins, amino acids, minerals, honey, royal jelly, and dietary fibers, and at least one selected from the group consisting of an acidifier, a sweetener, a flavoring agent, and natural fruit juice to manufacture a food in a form of powder, granules, tablets, capsules, jelly, cream, pap or drink.

6. The method as claimed in claim 4, further comprising the step of adding the final fermented product of the edible plants or the mixture of edible plants and edible animals with at least one selected from the group consisting of vitamins, amino acids, minerals, honey, royal jelly, and dietary fibers, and at least one selected from the group consisting of an acidifier, a sweetener, a flavoring agent, and natural fruit juice to manufacture a food in a form of powder, granules, tablets, capsules, jelly, cream, pap or drink.

7. A fermented product of edible plants or mixture of edible plants and edible animals, manufactured by the method as claimed in claim 5.

8. A nutritional supplementary food, a functional food, a health food or a tea, comprising the fermented product as claimed in claim 7.

9. The method as claimed in claim 2, further comprising the steps of:

sterilizing the liquid content at 80 to 85° C. for 10 to 30 minutes to obtain a liquid-final fermented product of the edible plants or the mixture of edible plants and edible animals; and compression-concentrating the liquid content to obtain an extract final fermented product of the edible plants or the mixture of edible plants and edible animals, or spray-drying or freeze-drying the liquid content to obtain an extract powder-final fermented product of the edible plants or the mixture of edible plants and edible animals.

10. The method as claimed in claim 2, further comprising the step of freeze-drying or hot-wind drying the solid content to obtain a powder final fermented product of the edible plants or the mixture of edible plants and edible animals.

11. A fermented product of edible plants or mixture of edible plants and edible animals, manufactured by the method as claimed in claim 6.

* * * * *